United States Patent
Kong et al.

(10) Patent No.: US 7,109,389 B2
(45) Date of Patent: Sep. 19, 2006

(54) PROCESS FOR THE DISPROPORTIONATION AND TRANSALKYLATION OF TOLUENE AND HEAVY AROMATICS

(75) Inventors: Dejin Kong, Shanghai (CN); Deqin Yang, Shanghai (CN); Huaying Li, Shanghai (CN); Hongli Guo, Shanghai (CN); Tian Ruan, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 552 days.

(21) Appl. No.: 10/392,457

(22) Filed: Mar. 19, 2003

(65) Prior Publication Data

US 2004/0186332 A1 Sep. 23, 2004

(51) Int. Cl.
*C07C 5/22* (2006.01)
(52) U.S. Cl. .............. 585/302; 585/304; 585/300; 585/475; 585/470
(58) Field of Classification Search ......... 585/302, 585/304, 300, 475, 470
See application file for complete search history.

(56) References Cited

U.S. PATENT DOCUMENTS 4,341,914 A 7/1982 Berger ................ 585/474

FOREIGN PATENT DOCUMENTS

| CN | 1235948 | 11/1999 |
|----|---------|---------|
| CN | 1340484 | 3/2000  |

OTHER PUBLICATIONS

The English version of CN 1340484A.*

* cited by examiner

*Primary Examiner*—Thuan D Dang
(74) *Attorney, Agent, or Firm*—Cohen, Pontani, Lieberman & Pavane

(57) ABSTRACT

A process for the disproportionation and transalkylation of toluene and the heavy aromatics comprises: subjecting a first stream of toluene, and a stream enriched in aromatics of nine carbon atoms to toluene disproportionation and transalkylation reactions in the presence of hydrogen in a first reaction zone to produce a first product mixture comprising benzene, aromatics of eight carbon atoms and heavy aromatics of ten and more carbon atoms; subjecting a second stream of toluene, and a stream enriched in heavy aromatics of ten and more carbon atoms to transalkylation reaction in the presence of hydrogen in a second reaction zone to produce a second product mixture comprising benzene, aromatics of eight carbon atoms and aromatics of nine carbon atoms; and isolating and recovering benzene and aromatics of eight carbon atoms from the first and second product mixtures.

12 Claims, 2 Drawing Sheets

PROCESS FOR THE DISPROPORTIONATION AND TRANSALKYLATION OF TOLUENE AND HEAVY AROMATICS

FIELD OF THE INVENTION

The present invention relates to a process for the disproportionation and transalkylation of toluene and heavy aromatics, and, in particular, to a process for reacting toluene with aromatics of nine and more carbon atoms to maximize $C_8$-aromatics yield.

BACKGROUND OF THE INVENTION

Processes for the disproportionation and transalkylation of toluene and heavy aromatics are important ways to produce aromatics of eight carbon atoms (referred to as $C_8A$ hereinafter). Up to date, as the typical and well-established process for this purpose, Tatoray process was developed in the late 1960s, MTDP process in the late 1980s, TransPlus and S-TDT processes recently.

In Tatoray process, toluene and aromatics of nine carbon atoms (referred to as $C_9A$ hereinafter) are used as the feed materials, with the level of heavy aromatics of ten and more carbon atoms (referred to as $C_{10^+}$ hereinafter) strictly controlled in the feedstock. In order to improve economic benefit and lower energy and material consumption, continued effort has been made to improve the Tatoray process, with focus on the catalyst. As a result, the overall performances of the catalyst, including space velocity, operation cycle, etc are improved. Meanwhile, the latitude in selecting the aromatics feedstock is also improved; for example, the aromatics feedstock with increased average molecular weight can be employed. The feedstock containing increased level of heavy aromatics facilitates the formation of $C_8A$; however, it necessitates an increased reaction temperature to achieve a certain conversion thereof. In that case, the yield of hydrocarbons of five and less carbon atoms (referred to as $C_{5^-}$ hereinafter) increases and the yield of the product of interest decreases correspondingly. In addition, owing to high activity of the employed catalyst, hydrodealkylation side reaction of aromatics is also accelerated, and the benzene (referred to as Ben hereinafter) yield increases. Accordingly, the $C_8A$ yield and $C_8A/Ben$ ratio of the product decrease, adversely affecting the overall economic benefit of the combined aromatics plant. In a combined aromatics plant, a unit of the disproportionation and transalkylation is indispensable for it produces $C_8A$. In view of this, an increased Ben or a decreased $C_8A$ yield obviously has a negative impact on the overall economic benefit of the combined aromatics plant. Besides, the increased level of heavy aromatics in the feedstock exacerbates coking on the catalyst, and shortens the operation cycle of this unit. In practice, the unit of the disproportionation and transalkylation cannot consume all the heavy aromatics produced in the combined aromatics plant. It follows that a large amount of heavy aromatics is not utilized in and inevitably discharged from the plant.

U.S. Pat. No. 4,341,914 disclosed a process of the disproportionation and transalkylation as shown in FIG. 1. In FIG. 1, the reference numeral 1 stands for xylene column I; 2 for heavy aromatics column; 3 for reaction zone; 4 for benzene column; 5 for toluene column; 6 for xylene column 11; 7 for $C_9A$ stream; 8 for $C_{8^+}A$ feed stream; 9 and 10 for toluene; 11 for benzene; 12 and 13 for $C_8A$; 17 and 19 for streams enriched in $C_{10^+}$; and 18 for stream enriched in $C_9A$. In this process, a portion of the resulting aromatics of ten carbon atoms (referred to as $C_{10}A$ hereinafter) is recycled to reaction zone along with the recycled $C_9A$ (stream 18), so as to inhibit production of $C_{10^+}$. The $C_{10^+}$ originally present in the $C_{8^+}A$ feed material, however, cannot be utilized; meanwhile, a portion of $C_9A$ originally present in the $C_{8^+}A$ feed material is discharged along with $C_{10^+}$ out of the plant from the bottom of heavy aromatics column (stream 19). On account of the nature of the employed catalyst, the latitude in selecting the feed materials is limited: it is required that the indan level in $C_9A$ stream (stream 7) be lower than 1 wt %.

Chinese Patent No. 98110859.8 disclosed a process of the disproportionation and transalkylation as shown in FIG. 2. In this figure, the reference numeral 1 stands for xylene column I; 2 for heavy aromatics column; 3 for reaction zone; 4 for benzene column; 5 for toluene column; 6 for xylene column II; 7 for o-xylene column; 8 for $C_{8^+}A$ raw material; 12 and 13 for $C_8A$; 9 for toluene; 14 for stream enriched in $C_9A$; 15 for the heavy hydrocarbons of eleven and more carbon atoms (referred to as $C_{11^+}$ hydrocarbons hereinafter); 16 for recycled toluene; 17 for benzene; 19 for o-xylene; and 20 for $C_{9^+}A$ with or without o-xylene. This process is free from many of the disadvantages of the prior art in that it allows use of raw materials containing increased level of indane and $C_{10}A$, and achieves increased conversion of $C_{10^+}$ heavy aromatics. The process, however, suffers such disadvantages as shortened catalyst service life, leading to a mismatch with the operation life of the plant, which is becoming longer and longer. In addition, the process achieves little in improving $C_8A$ yield.

To date, the prior art has been seeking to improve the existing processes for the disproportionation and transalkylation of toluene and heavy aromatics by modifying the catalyst in terms of one or more aspects or by altering the technical measures to isolate the reaction products. For example, attempt has been made to enhance the transalkylation capability of the catalyst with respect to heavy aromatics. It fails, however, to achieve a balanced results of ample latitude in selecting feed material of high level of heavy aromatics, high yield of $C_8A$ and low yield of light hydrocarbons.

The prior art exerts rigid control over the amount of $C_{10^+}$ hydrocarbons in the raw materials to increase the operation life of the catalyst. At present, however, it is possible for the raw material to include some $C_{10^+}$ hydrocarbons as a result of progress in catalyst technology. The raw material containing an amount of $C_{10^+}$ hydrocarbons increases yield of the product of interest under the conditions of increased conversion and higher space velocity. All the same, most of $C_{10^+}$ hydrocarbons still cannot be fully utilized.

Moreover, the patents mentioned above all focus on processing aromatic raw materials without regard for the role of the unit of the disproportionation and transalkylation, which produces $C_8A$ in a combined aromatics plant. In other words, the above patents fail to pay sufficient attention to the economic benefit of the reaction products, represented by the ratio of $C_8A/Ben$ of the products. Increased $C_8A$ yield will immediately raise the pX yield of the combined aromatics plant and better economic benefits will be achieved.

Thus, in the field of the disproportionation and transalkylation of toluene and heavy aromatics, there exists a need for a new process which is free from the disadvantages of the prior art, i.e. low utilization of heavy aromatics in a combined aromatic plant, a limited $C_8A$ yield and a rigid control over the selection of the raw materials. By employing such a process, ample latitude in selecting materials, a decreased formation of light hydrocarbons, full utilization of heavy aromatics and increased $C_8A$ yield are achieved.

SUMMARY OF THE INVENTION

It is therefore an object of the present invention to provide a process for the disproportionation and transalkylation of toluene and heavy aromatics comprising the following steps:

a) providing respectively the raw materials: the first stream of toluene, the second stream of toluene, a stream enriched in aromatics of nine carbon atoms and a stream enriched in heavy aromatics of ten and more carbon atoms;

b) feeding the first stream of toluene, and the stream enriched in aromatics of nine carbon atoms to the first reaction zone; and feeding the second stream of toluene, and the stream enriched in $C_{10^+}$ hydrocarbons to the second reaction zone;

c) subjecting the first stream of toluene, and the stream enriched in aromatics of nine carbon atoms to toluene disproportionation and transalkylation reactions in the presence of hydrogen in the first reaction zone to produce a product mixture comprising benzene, aromatics of eight carbon atoms and heavy aromatics of ten and more carbon atoms ($C_{10^+}$); and subjecting the second stream of toluene, and the stream enriched in heavy aromatics of ten and more carbon atoms to transalkylation reaction in the presence of hydrogen in the second reaction zone to produce a product mixture comprising benzene, aromatics of eight carbon atoms and aromatics of nine carbon atoms; and d) isolating and recovering benzene and aromatics of eight carbon atoms from the product mixtures from step c).

MODE OF CARRYING OUT THE INVENTION

Figure 1:
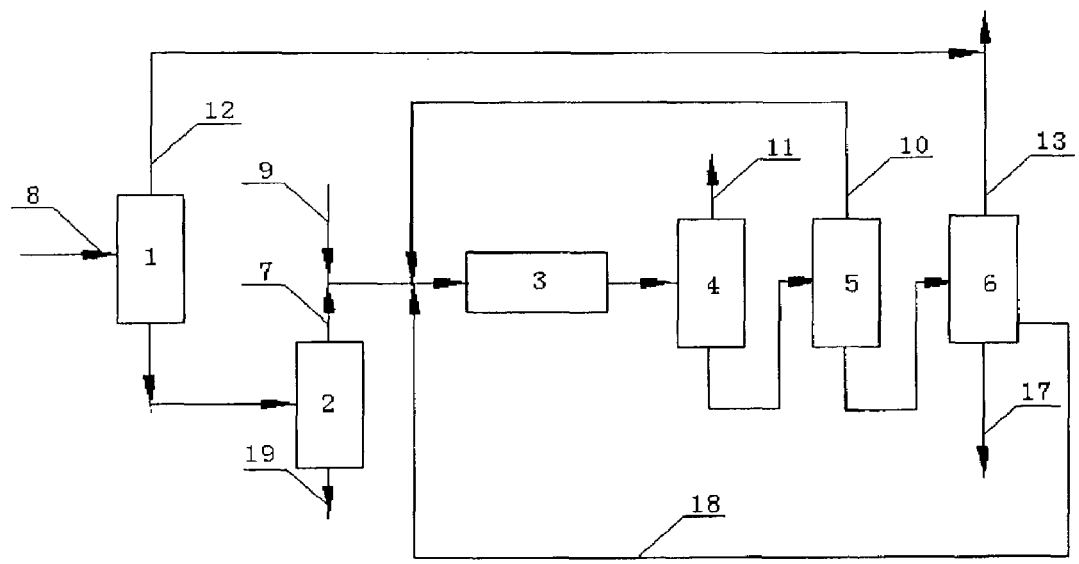
FIG. 1 is a flow sheet of the process of U.S. Pat. No. 4,341,914.
Figure 2:
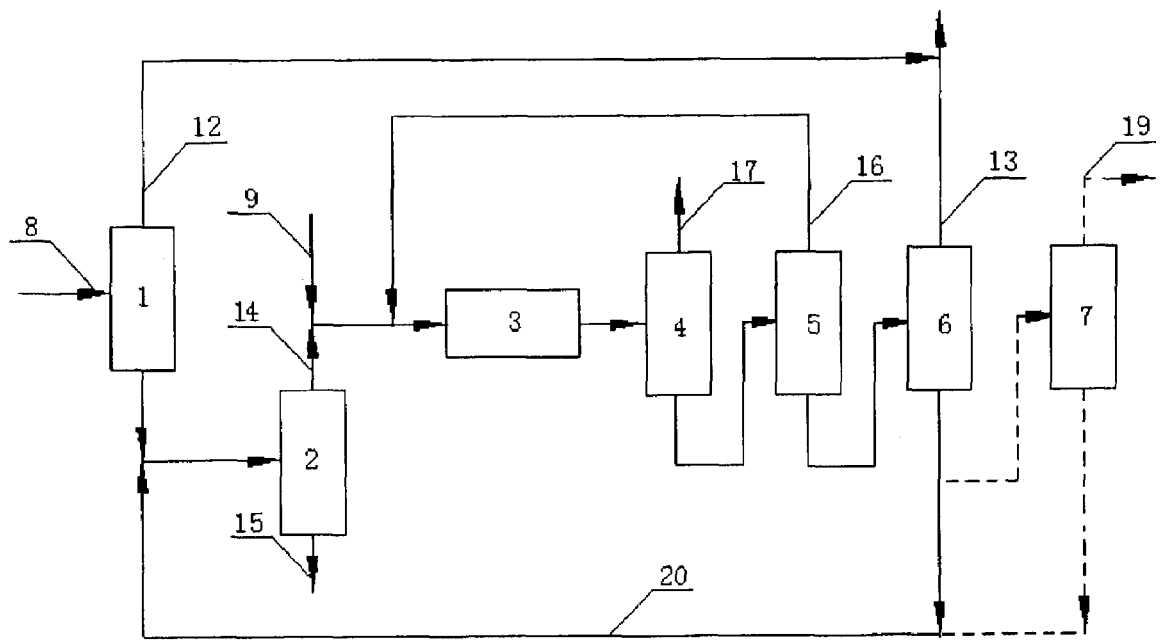
FIG. 2 is a flow sheet of the process of CN 98110859.8.

The process of the invention comprises the steps of a) providing raw materials, b) feeding the raw materials to the reaction zones, c) reacting the raw materials and d) isolating the product mixture to obtain intended products.

In step a), raw materials, including the first stream of toluene, the second stream of toluene, a stream enriched in aromatics of nine carbon atoms and a stream enriched in $C_{10^+}$, are provided. Such materials are readily available from many sources. In a preferred embodiment, toluene, the stream enriched in $C_9A$ and the stream enriched in $C_{10^+}$ are obtained by isolating a $C_{6^+}A$ (aromatics of six and more carbon atoms) stream from the Pt-reformation unit of a combined aromatics plant. Thus, aromatics feed that contains benzene, toluene, $C_8A$, $C_9A$, indan and $C_{10^+}$ hydrocarbons is separated in a separation unit into a benzene stream, a toluene stream, a $C_8A$ stream, a stream enriched in $C_9A$ and a stream enriched in $C_{10^+}$ hydrocarbons, of which the stream enriched in $C_9A$ is allowed to contain 0–30% $C_{10^+}$ and 0–5% indan by weight, and the stream enriched in $C_{10^+}$ to contain $C_9A$ of 0–20% by weight.

In step b), the first stream of toluene and a stream enriched in $C_9A$, together with or separate from each other, are fed to the first reaction zone. Meantime, the second stream of toluene and a stream enriched in $C_{10^+}$, together with or separate from each other, are fed to the second reaction zone.

For example, the feed material of the first reaction zone comprises by weight 10–90% of toluene, 10–90% of $C_9A$, 0–5% of indan and 0–5% of $C_{10}A$, and the feed material of the second reaction zone comprises toluene and $C_{10^+}$ in a ratio by weight of 0/100–95/5 of toluene/$C_{10^+}$.

In step c), the first stream of toluene and the stream enriched in $C_9A$ are subjected to the disproportionation and transalkylation reactions in the presence of hydrogen in the first reaction zone; the reactions produce a product mixture comprising benzene, $C_8A$ and $C_{10^+}$ hydrocarbons. In the meantime, the second stream of toluene and the stream enriched in $C_{10^+}$ are subjected to transalkylation reaction in the presence of hydrogen in the second reaction zone; the reaction produces a product mixture comprising benzene, $C_8A$ and $C_9A$. The reactions in the first and second reaction zones proceed in the presence of catalysts. The catalysts employed in the first and second reaction zones can be one or more catalysts known in the art for these purposes, for example, a metal-containing zeolite. Of the catalyst, the metal can be one or more selected from the group consisting of Bi, Mo, Fe, Co, Ni, Pt, Ag, Pd, and Au, and the zeolite can be one or more selected from the group consisting of Y-type zeolite, mordenite, β-zeolite and ZSM-type zeolite. The catalysts used in the first and second reaction zones can be the same catalyst, or they can be different catalysts. In a preferred embodiment of the invention, the catalyst employed in the first reaction zone is a bismuth-containing macropore zeolite, for example, bismuth-containing mordenite or βzeolite; and the catalyst employed in the second reaction zone is a molybdenum-containing macropore zeolite, for example, molybdenum-containing mordenite or βzeolite. During reactions, in the first and second reaction zones, the pressure is 1.0–5.0 MPa, the temperature is 300–480□, and hydrogen/hydrocarbon molar ratio is 1–10. The space velocity by weight is maintained at 0.8–8 $h^{-1}$ in the first reaction zone, and at 0.5–8 $h^{-1}$ in the second reaction zone.

In step d), following the reactions in step c), the product mixtures from step c) are isolated to obtain benzene and $C_8A$. The product mixtures from the first reaction and second reaction zones are isolated separately; alternatively, the product mixtures from the first and second reaction zones can also be combined and then isolated. In a preferred embodiment, benzene, toluene, $C_8A$, the stream enriched in $C_9A$ and the stream enriched in $C_{10^+}$ hydrocarbons are also isolated from the product mixtures, and toluene, the stream enriched in $C_9A$ and the stream enriched in $C_{10^+}$ hydrocarbons are recycled to step a) and/or step b) to serve as raw materials. The isolation of the product mixtures can be carried out in accordance with the known techniques.

In the process of present invention, two reaction zones are adopted, and toluene is divided into two streams, which are fed to these two reaction zones. Accordingly, a reduced toluene/$C_9A$ ratio results in the first reaction zone, and toluene disproportionation is decreased in favor of transalkylation reaction between toluene and $C_9A$. As a result, benzene formation decreases, while $C_8A$ formation increases, i.e., $C_8A$ yield increases. In addition, under the reaction conditions of the first reaction zone, the catalyst shows the perfect catalytic properties, including less restriction on the level of indan in the raw materials. The formed $C_{10^+}$ hydrocarbons may be separated and recycled to step a) and/or b) and then be fed to the second reaction zone.

In the second reaction zone, toluene and the stream enriched in $C_{10^+}$ hydrocarbons undergo transalkylation reaction to provide lighter aromatics from the heavy aromatics, as opposed to the conventional aromatics-lightening techniques, which usually includes hydro-dealkylation of the heavy aromatics. Owing to the transalkylation reaction, the formation of light hydrocarbons is also inhibited, and an increased $C_8A$ yield is obtained. Thus, the raw materials are utilized in a more economically efficient way. The reaction in the second reaction zone mainly produces $C_8A$ and $C_9A$ as well as benzene. The formed benzene and $C_8A$, after isolation, can be recovered as final products; the formed $C_9A$ may be isolated and recycled, used as the feedstock to the first reaction zone.

In the first reaction zone, the major reactions include toluene disproportionation and transalkylation of $C_9A$, as described in the following scheme:

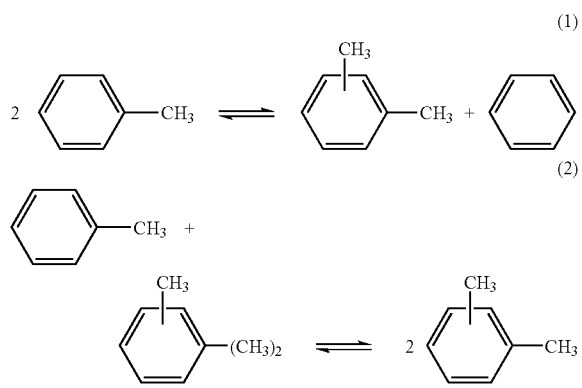

In addition, the side reactions include hydro-dealkylation of aromatics and disproportionation of $C_9A$:

$$\langle \rangle\!-\!R + H_2 \rightleftharpoons \langle \rangle + RH \quad (3)$$

$$2C9A \rightleftharpoons C8A + C10 \quad (4)$$

In light of the chemical equilibrium, under the reaction conditions of the present process, the composition of the reactants feed, including the Toluene/$C_9A$ ratio, has an impact on the conversions of the reactants and the yield of the products. For example, Toluene/$C_9A$ ratio has a direct influence on the ratio of $C_8A$/Ben in the product stream: the higher the ratio of Toluene/$C_9A$, the less the ratio of $C_8A$/Ben; on the contrary, the lower the ratio of Toluene/$C_9A$, the higher the ratio of $C_8A$/Ben.

Theoretically, if only toluene were used as the raw material, there would only toluene disproportionation occur, resulting in a Ben/$C_8A$ molar ratio of 1:1 in the products. After $C_9A$ is added into the feed, however, the yield of $C_8A$ increases. In particular, when Toluene/$C_9A$ molar ratio is 1:1 in the feed, a maximum $C_8A$ yield is obtained.

In the second reaction zone, since the raw material is comprised of more complex $C_{10^+}$ hydrocarbons as well as toluene, the reaction system becomes more complex, and varies with changes in feed composition. According to results from a series of test runs, when the amount of toluene is greater than that of $C_{10^+}$ hydrocarbons, reactions of toluene disproportionation and transalkylation between toluene and $C_{10^+}$ hydrocarbons may be considered as the main reactions with major products including benzene, $C_8A$ and $C_9A$:

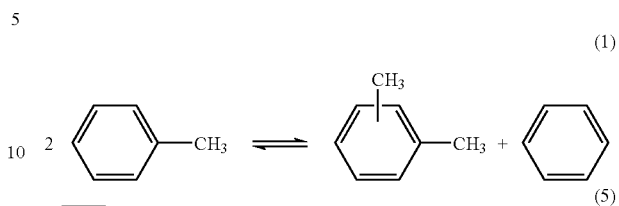

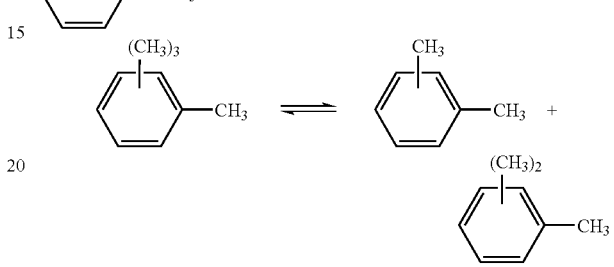

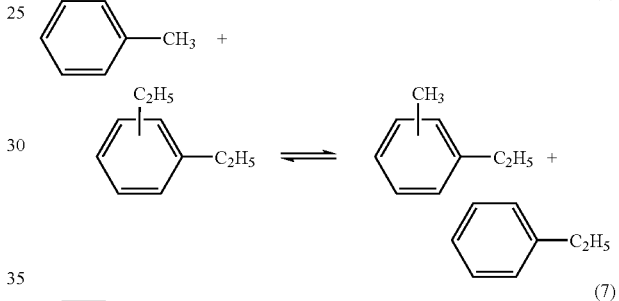

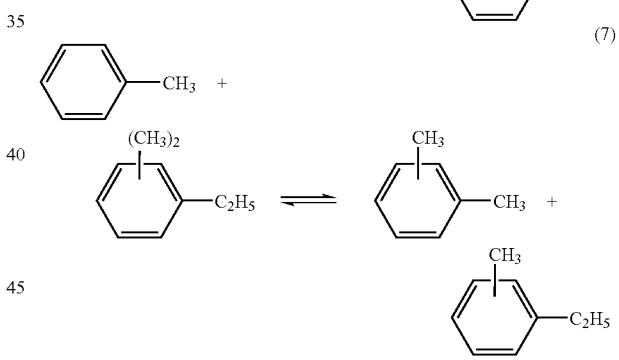

As the ratio of toluene/$C_{10^+}$ becomes less than 1, the hydro-dealkylation of heavy aromatics becomes the dominant reaction. In practice, adjusting the feed flow rate of toluene can control the ratio of toluene/$C_{10^+}$.

It can thus be seen from the above that, by diverting a portion of toluene feed to the second reaction zone, Toluene/$C_9A$ ratio in the first reaction zone may be decreased, which benefits the transalkylation reaction between toluene and $C_9A$. Accordingly, benzene formation is decreased and $C_8A$ formation is enhanced. In the mean time, because of the decreased toluene content, disproportionation of $C_9A$ is enhanced, giving the intended product $C_8A$ as well as $C_{10}A$, which is recycled to the second reaction zone. In the second reaction zone, toluene and $C_{10}$+hydrocarbons mainly undergo transalkylation reaction, forming $C_8A$ and $C_9A$, in which $C_9A$ is one of the raw materials of the first reaction zone. The $C_9A$ formed in the second reaction zone is recycled to the first reaction zone and will further decrease the Toluene/C$_9$A ratio in the first reaction zone, and thus increase the C$_8$A yield. Thus, it can be seen that dividing toluene stream and feeding the divided streams to different reaction zones help to enhance the C$_8$A yield. Besides, the C$_{10}$A produced by C$_9$A disproportionation in the first reaction zone serves as a raw material of the second reaction zone; the C$_9$A formed by transalkylation reaction in the second reaction zone serves as a raw material of the first reaction zone. What is more, in the second reaction zone, the process of producing lighter hydrocarbons from some higher heavy aromatics, such as C$_{11+}$ hydrocarbons, is different from the conventional hydro-dealkylation technique, such as those described in U.S. Pat. No. 4,172,813. In the instant process, alkyl groups are transferred from heavy aromatics to lighter aromatics, forming C$_8$A or C$_9$A, with the result that the formation of lighter paraffin is substantially lowered, while more C$_8$A and C$_9$A are produced. This is proved by laboratory data.

In view of the overall process of the invention, it can be found that, by reacting C$_9$A and C$_{10+}$ in different reaction zones, C$_{10+}$ can be used as raw materials, and there is no need to discharge C$_{10+}$ out of the plant. In addition, as C$_{10+}$ is used as a raw material, the average molecular weight of feed is increased, which in turn enhances the formation of C$_8$A and hence an increased C$_8$A/Ben ratio of the product. Experiment data also confirmed that total C$_8$A yield has been improved by a big margin using the process of the present invention.

Figure 3:
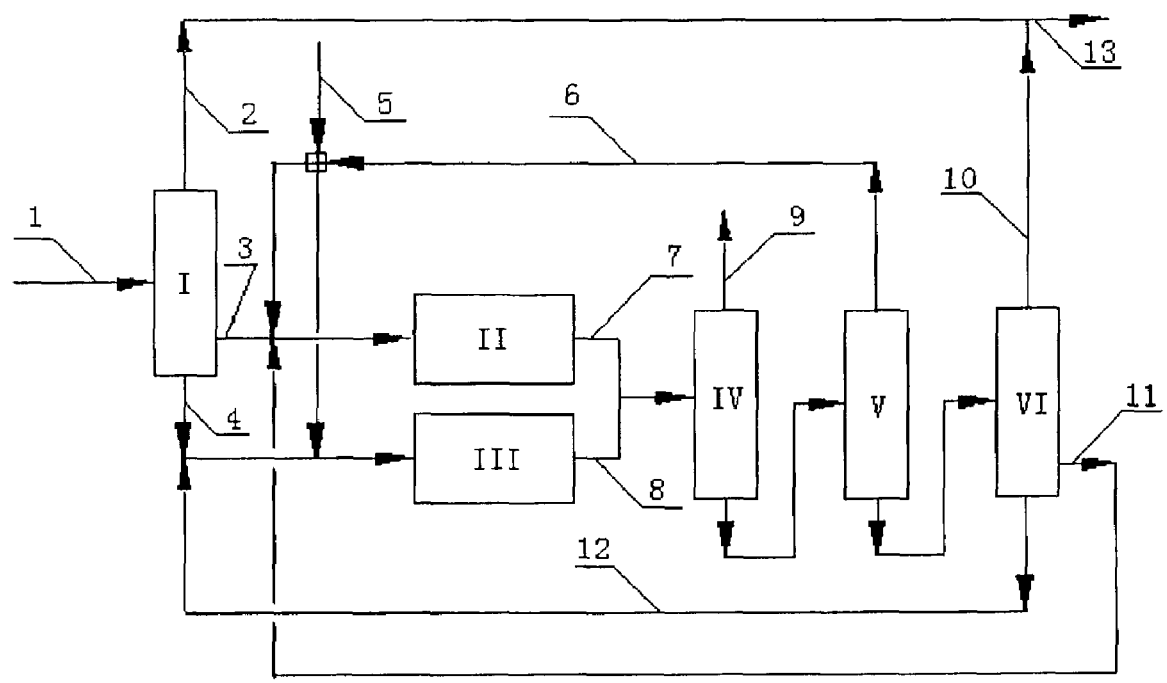
FIG. 3 is the flow sheet of a preferred embodiment of the present invention.

FIG. 3 shows a preferred embodiment of the process of the invention. In such an embodiment, the process is carried out in a unit of the disproportionation and transalkylation within a combined aromatics plant. Referring to FIG. 3, the unit comprises xylene column I, first reaction zone II, the second reaction zone III, benzene column IV, toluene column V and xylene column VI. In the unit, a C$_8$A-enriched C$_{8+}$A feed stream 1 is separated in xylene column I into C$_8$A stream 2 at the top, C$_9$A-rich stream 3 as a side stream and C$_{10+}$-rich stream 4 at the bottom. Stream 3 is combined with incoming toluene, and then enters the first reaction zone. In the first reaction zone, toluene and C$_9$A undergo toluene disproportionation and transalkylation reactions in the presence of hydrogen, producing a reaction effluent 7. On the other hand, stream 4 is mixed with incoming toluene and then enters the second reaction zone. In the second reaction zone, toluene and C$_{10+}$ hydrocarbons undergo transalkylation reaction in the presence of hydrogen, forming a reaction effluent enriched in benzene, C$_8$A and C$_9$A. After combined, streams 7 and 8 are separated into benzene (stream 9), toluene (stream 6), C$_8$A (stream 10), C$_9$A-rich streams 11 and C$_{10+}$-rich stream 12. Streams 11 and 3, mixed with the toluene, constitute the feed to the first reaction zone, and streams 12 and 4, mixed with toluene, constitute feed to the second reaction zone. As the main product, the C$_8$A stream 13, i.e. the combined stream of streams 10 and 2, is discharged out of the unit for further processing. The formed benzene (stream 9) is discharged out of the unit as a side product without further processing. The fresh toluene (stream 5) from outside the unit is merged with recycling toluene (stream 6), then is divided into two portions and fed to the first and second reaction zones respectively. Carried out in accordance with this embodiment, the process of present invention constitutes a clean process, which is pursued in the 21st century.

The present invention will be further illustrated in the following non-limiting examples.

Examples 1 to 4 Toluene and the raw material enriched in C$_9$A were subjected to toluene disproportionation and transalkylation reactions. The reactions were carried out in a fixed bed reactor in the presence of hydrogen and bismuth-containing macropore zeolite catalyst. The reactor used had a diameter of 25 mm and a length of 1000 mm, made of stainless steel. Glass beads 3 mm in diameter were evenly filled at both the top and the bottom of the bed for the purpose of gas distribution and support. 20 g of bismuth-containing marcoporous zeolite catalyst was loaded into the reactor. Aromatics raw materials and hydrogen were, after mixing up, passed downflow through the catalyst bed, in which toluene disproportionation and transalkylation of toluene and C$_9$A occurred. Benzene and C$_8$A were produced.

TABLE 1

Results from disproportionation and transalkylation between toluene and C$_9$A

| | Examples | | | |
|---|---|---|---|---|
| | 1 | 2 | 3 | 4 |
| Active component of the catalyst | A | B | A | B |
| SiO$_2$/Al$_2$O$_3$ of the zeolite used, mol/mol | 17.2 | 22.5 | 35.1 | 37.8 |
| Temperature, | 340 | 380 | 430 | 405 |
| Pressure MPa | 2.5 | 3.0 | 3.5 | 4.0 |
| Space velocity, h$^{-1}$ | 1.0 | 1.5 | 4.5 | 3.0 |
| Hydrogen/hydrocarbon ratio, mole/mole | 6.0 | 3.0 | 9.0 | 10.0 |
| Feed Tol:C$_9$A, by weight | 60:40 | 55:45 | 50:50 | 40:60 |
| Composition of the feed, wt % | | | | |
| NA | 0.03 | 0.02 | 0.02 | 0.02 |
| Ben | 0.02 | 0.02 | 0.02 | 0.01 |
| Tol | 57.16 | 53.32 | 47.47 | 37.82 |
| C$_8$A | 0.56 | 0.50 | 0.60 | 0.42 |
| C$_9$A | 38.16 | 42.90 | 47.26 | 56.00 |
| IND | 0.52 | 0.61 | 1.06 | 1.81 |
| C$_{10+}$ | 3.55 | 2.63 | 3.57 | 3.92 |
| Σ | 100.00 | 100.00 | 100.00 | 100.00 |
| Composition of the product, wt % | | | | |
| NA | 2.32 | 2.54 | 2.77 | 2.40 |
| Ben | 11.41 | 10.42 | 9.43 | 8.17 |
| Tol | 36.10 | 35.11 | 34.12 | 32.86 |
| C$_8$A | 33.96 | 34.27 | 34.58 | 34.30 |
| C$_9$A | 13.06 | 14.33 | 15.20 | 17.61 |
| IND | 0.04 | 0.05 | 0.04 | 0.05 |
| C$_{10+}$ | 3.11 | 3.28 | 3.86 | 4.61 |
| Σ | 100.00 | 100.00 | 100.00 | 100.00 |

Note:
A stands for 1.5% bismuth-containing mordenite; and
B for 2.0% bismuth-containing β-zeolite

EXAMPLES 5 TO 7

Toluene and the raw material enriched in C$_{10+}$ hydrocarbons were subjected to transalkylation reaction. The reaction was carried out in a fixed bed reactor in the presence of hydrogen and molybdenum-containing macropore zeolite catalyst. The reactor used had a diameter of 25 mm and a length of 1000 mm, made of stainless steel. Glass beads 3 mm in diameter were evenly filled at both the top and the bottom of the catalyst bed for the purpose of gas distribution and support. 20 g of molybdenum-containing macropore zeolite catalyst was loaded into the reactor. Aromatics raw materials and hydrogen were, after mixing up, passed downflow through the catalyst bed, in which transalkylation occurred. Benzene, $C_8A$ and $C_9A$ were formed by the reaction between toluene and $C_{10^+}$ hydrocarbons.

TABLE 2

Transalkylation reaction between toluene and $C_{10^+}$

|  | Examples | | |
| --- | --- | --- | --- |
|  | 5 | 6 | 7 |
| Active component of the catalyst* | A | B | B |
| $SiO_2/Al_2O_3$ of the zeolite used, mol/mol | 45.5 | 22 | 40 |
| Temperature, °C. | 340 | 400 | 450 |
| Pressure MPa | 2.0 | 3.0 | 4.0 |
| Space velocity, $h^{-1}$ | 0.8 | 3.0 | 5.0 |
| Hydrogen/hydrocarbon ratio, mole/mole | 2 | 6 | 8 |
| Feed Tol:$C_{10^+}$, by weight | 90:10 | 70:30 | 50:50 |
| Composition Of the feed, wt % | | | |
| NA | 0.01 | 0.00 | 0.00 |
| Ben | 0.30 | 0.26 | 0.19 |
| Tol | 88.88 | 67.37 | 49.50 |
| $C_8A$ | 0.35 | 0.47 | 0.36 |
| $C_9A$ | 0.46 | 0.25 | 1.01 |
| IND | 0.02 | 0.22 | 0.47 |
| $C_{10^+}$ | 9.98 | 31.43 | 48.47 |
| Σ | 100.00 | 100.00 | 100.00 |
| Composition of the product, wt % | | | |
| NA | 2.50 | 3.27 | 6.63 |
| Ben | 13.61 | 8.21 | 8.24 |
| Tol | 60.44 | 50.70 | 39.50 |
| $C_8A$ | 14.21 | 20.74 | 20.15 |
| $C_9A$ | 6.87 | 8.84 | 10.43 |
| IND | 0.02 | 0.03 | 0.05 |
| $C_{10^+}$ | 2.35 | 8.21 | 15.00 |
| Σ | 100.00 | 100.00 | 100.00 |

Note:
A stands for 2.5% molybdenum-containing mordenite; and
B for 1.8% molybdenum-containing β-zeolite

COMPARATIVE EXAMPLE 1

Based on the data described in example 1, a typical disproportionation and transalkylation reaction between toluene and $C_9A$ was conducted. In the reactor feed, a ratio of toluene/$C_9A$ of 60:40 was used. When a feed flow rate of 100 W/T (unit weight unit time) was used, consumed amount of toluene (ΔTol) and consumed amount of $C_9A$ (Δ$C_9A$) in the reaction (i.e., fresh feed materials) are as follows:

ΔTol=57.16–36.10=21.06(W/T)
Δ$C_9A$=38.16–13.06=25.10(W/T)
ΔTol/Δ$C_gA$=1/1.2

The amounts above correspond to those consumed in a unit of the disproportionation and transalkylation of a typical combined aromatics plant.

The amounts of the products are as the following:
the amount of benzene formed: ΔBen=11.41–0.02=11.39 (WIT)
the amount of benzene formed: Δ$C_8A$=33.96–0.56=33.40 (WIT)

Thus, in a typical toluene disproportionation and transalkylation process, when feed flow rates of fresh toluene and fresh $C_9A$ are 21.06 W/T and 25.10 W/T respectively, 11.39 W/T benzene and 33.40 W/T $C_8A$ were produced after complete reaction.

COMPARATIVE EXAMPLE 2

In this example, the formations of benzene and $C_8A$ are investigated using the same feed flow rates of fresh toluene and fresh $C_9A$, that is, 21.06 W/T and 25.10 W/T respectively.

A portion of toluene and all $C_9A$ coming from outside the unit, and the $C_9A$ formed in the second reaction zone, as the fresh feedstock, underwent toluene disproportionation and transalkylation in the first reaction zone. Another portion of toluene coming from outside the unit and the $C_{10^+}$ hydrocarbons formed in the first reaction zone as well as $C_{10^+}$ hydrocarbons from $C_{8^+}A$ raw material, as the fresh feedstock, underwent transalkylation between toluene and $C_{10^+}$ in the second reaction zone. Composition of feed of the first reaction zone was the same as in example 2: the toluene/$C_9A$ ratio was 55:45; composition of feed of the second reaction zone was the same as in example 6: the toluene/$C_{10^+}$ ratio was 70:30. The total of fresh toluene feed of both the first and second reaction zones was 21.06 WIT. $C_9A$ feed to first reaction zone was equal to the fresh $C_9A$ feed plus withdrawal of $C_9A$ from the second reaction zone. Results from computer simulation are summarized in table 3.

TABLE 3

A mass balance according to this invention (unit: W/T)

| Components | First reaction zone | Second reaction zone | The inventive process |
| --- | --- | --- | --- |
| Raw materials reacted | | | |
| Tol | 17.25 | 3.81 | 21.06 |
| $C_9A$* | 27.06* | / | 27.06 |
| $C_{10^+}$ | / | 5.35 | 5.35 |
| Products produced | | | |
| Ben | 9.85 | 1.82 | 11.67 |
| $C_8A$ | 31.99 | 4.63 | 36.62 |
| $C_9A$ | / | 1.96 | 1.96 |
| $C_{10^+}$ | 0.62 | / | / |

Note:
$C_9A$ entering first reaction zone is 27.06 W/T. The 1.96 W/T surplus over the amount from outside the unit of 25.10 W/T came from the second reaction zone, that is, the $C_9A$ formed by transalkylation between toluene and $C_{10^+}$.

It can be seen from the above that the shortcomings existing with an combined aromatics plant of the prior art, including low utilization of heavy aromatics, restricted $C_8A$ yield and higher formation of lighter hydrocarbons and less flexibility or stringent requirement on the selection of raw materials are all solved by the present invention. This process achieves ample latitude in selecting raw materials, less formation of lighter hydrocarbons and complete utilization of heavy aromatics and an increased $C_8A$ yield. From the comparative examples 1 and 2, it can be concluded that given the same amount of toluene and $C_9A$ consumed, 11.67 W/T of benzene and 36.62 W/T of $C_8A$ are produced in the process of the present invention, representing increases of 2.5% and 9.6% respectively compared with conventional process for toluene disproportionation and transalkylation.

What is claimed is:
1. A process for the disproportionation and transalkylation of toluene and heavy aromatics, comprising the following steps:
   a) providing raw materials: a stream of toluene, a stream enriched in aromatics of nine carbon atoms and a stream enriched in heavy aromatics of ten and more carbon atoms, wherein the stream of toluene is divided into a first stream of toluene and a second stream of toluene;

b) feeding the first stream of toluene, and the stream enriched in aromatics of nine carbon atoms to a first reaction zone; and feeding the second stream of toluene and the stream enriched in heavy aromatics of ten and more carbon atoms to a second reaction zone;

c) subjecting the first stream of toluene, and the stream enriched in aromatics of nine carbon atoms to toluene disproportionation and transalkylation reactions in the presence of hydrogen in the first reaction zone to produce a first product mixture comprising benzene, aromatics of eight carbon atoms and heavy aromatics of ten and more carbon atoms; and subjecting the second stream of toluene, and the stream enriched in heavy aromatics of ten and more carbon atoms to transalkylation reaction in the presence of hydrogen in the second reaction zone to produce a second product mixture comprising benzene, aromatics of eight carbon atoms and aromatics of nine carbon atoms; and d) isolating and recovering benzene and aromatics of eight carbon atoms from the first and the second product mixtures from step c).

2. The process of claim 1, further comprising isolating from the first and second product mixtures from step c) and recycling respectively to step a) and/or step b) toluene, aromatics of nine carbon atoms and heavy aromatics of ten and more carbon atoms.

3. The process of claim 1, wherein the raw materials provided in step a) are obtained by isolating a stream enriched in aromatics of six and more carbon atoms from a combined aromatics plant.

4. The process of claim 1, wherein the stream enriched in aromatics of nine carbon atoms contains indan.

5. The process of claim 1, wherein the first and second reaction zones employ one or more zeolites as catalysts, wherein the zeolites comprise metal.

6. The process of claim 5, wherein the first and second reaction zones employ different catalyst from each other.

7. The process of claim 5, wherein the metal is one or more selected from the group consisting of Bi, Mo, Fe, Co, Ni, Pt, Ag, Pd, and Au, and the zeolites are one or more selected from the group consisting of Y-type zeolite, mordenite, β-zeolite and ZSM-type zeolite.

8. The process of claim 5, wherein the catalyst used in the first reaction zone is a macropore zeolite comprising bismuth; and the catalyst used in the second reaction zone is a macropore zeolite comprising molybdenum.

9. The process of claim 1, wherein the first reaction zone has a pressure of 1.0–5.0 MPa, a temperature of 300–480° C., a hydrogen and hydrocarbon molar ratio of 1–10, and space velocity by weight of 0.8–8 $h^{-1}$.

10. The process of claim 1, wherein the second reaction zone has a pressure of 1.0–5.0 MPa, a temperature of 300–480° C., a hydrogen and hydrocarbon molar ratio of 1–10, and a space velocity by weight of 0.5–8 $h^{-1}$.

11. The process of claim 1, wherein the feed material to the first reaction zone comprises by weight 10–90% of toluene, 10–90% of aromatics of nine carbon atoms, 0–5% of indan and 0–5% of heavy aromatics of ten carbon atoms.

12. The process of claim 1, wherein the feed material to the second reaction zone comprises toluene and the heavy aromatics of ten and more carbon atoms in a ratio by weight of about 50:50–95/5 of toluene and the heavy aromatics of ten and more carbon atoms.

* * * * *